United States Patent [19]
Koch

[11] Patent Number: 5,240,624
[45] Date of Patent: Aug. 31, 1993

[54] BORON-CONTAINING COMPOSITIONS AND LUBRICANTS CONTAINING THEM

[75] Inventor: Frederick W. Koch, Willoughby Hills, Ohio

[73] Assignee: The Lubrizol Corporation, Wickliffe, Ohio

[21] Appl. No.: 796,911

[22] Filed: Nov. 22, 1991

Related U.S. Application Data

[63] Continuation of Ser. No. 616,758, Nov. 19, 1990, abandoned, which is a continuation of Ser. No. 443,892, Nov. 30, 1989, abandoned, which is a continuation of Ser. No. 266,313, Oct. 31, 1988, abandoned, which is a continuation of Ser. No. 62,286, Jun. 12, 1987, abandoned, which is a continuation of Ser. No. 484,660, Apr. 13, 1983, abandoned, which is a continuation-in-part of Ser. No. 342,635, Jan. 26, 1982, abandoned.

[51] Int. Cl.⁵ ............................................ C10M 129/14
[52] U.S. Cl. .................................. 252/49.6; 252/400.4
[58] Field of Search ............................ 252/49.6, 400.4

[56] References Cited

U.S. PATENT DOCUMENTS

| | | | |
|---|---|---|---|
| 2,962,446 | 11/1960 | Cook | 252/49.6 |
| 2,975,134 | 3/1961 | Cook | 252/49.6 |
| 3,479,294 | 11/1969 | Weck | 252/182 |
| 4,053,428 | 10/1977 | Pindar et al. | 252/49.6 |
| 4,147,643 | 4/1979 | Pindar et al. | 252/52 R |

OTHER PUBLICATIONS

Smallheer et al; Lubricant Additives, 1967 pp. 9-11.

*Primary Examiner*—Jacqueline V. Howard
*Attorney, Agent, or Firm*—Joseph P. Fischer; Frederick D. Hunter; James L. Cordek

[57] ABSTRACT

Boron-containing compositions are prepared by the reaction of boric acid with the condensation product (which may be formed in situ) of a hydroxyaromatic compound)preferably a phenol) with an aromatic or aliphatic aldehyde (preferably formaldehyde). These compositions are useful as lubricant additives to inhibit oxidation, improve extreme pressure properties and decrease fuel consumption. They are especially useful as oxidation inhibitors in gear and bearing lubricants containing substantial amounts of sulfur and phosphorus compounds.

32 Claims, No Drawings

BORON-CONTAINING COMPOSITIONS AND LUBRICANTS CONTAINING THEM

This application is a continuation of Ser. No. 07/616,758 filed on Nov. 19, 1990, which is continuation of Ser. No. 07/443,892 filed on Nov. 30, 1989, both now abandoned, which is a continuation of Ser. No. 07/266,313 filed on Oct. 31, 1988, abandoned, which is a continuation of Ser. No. 07/062,286 filed on Jun. 12, 1987, abandoned, which is a continuation of Ser. No. 06/484,660 filed on Apr. 13, 1983, abandoned, which is a continuation-in-part of Ser. No. 06/342,635 filed on Jan. 26, 1982, abandoned.

This invention relates to compositions useful as additives for lubricants, especially industrial gear oils; to a method for the preparation of such compositions; and to additive concentrates and lubricants containing them. In their most general sense, the compositions of this invention are boron-containing compositions prepared by reaction, at a temperature within the range of about 70°–250° C.:

(A) at least one compound of the formula

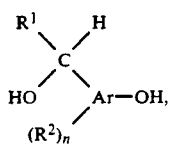

Formula I wherein $R^1$ is hydrogen, a lower alkyl-based radical or an aromatic radical, $R^2$ is hydrogen or an aliphatic hydrocarbon-based radical free from acetylenic unsaturation, n is a number from 1 to 4, and Ar is an aromatic hydrocarbon-based radical; and (B) at least one of boric acid, boron trioxide, boron halides and esters of boric acid.

Recent developments in the area of machinery operation have material increased the demands made on lubricants for use in such machinery. For example, increases in the price of gasoline and other fuels and sporadic shortages of such fuels have increased the necessity for lubricant additives which promote fuel economy. In the area of gear lubricants, it has been necessary to develop additives which improve operation under conditions of extreme pressure.

A further area of increasing demand on gear and bearing lubricants, particularly for industrial use, relates to formation of deposits through oxidation. Such deposits frequently form, especially in lubricants containing substantial amounts of phosphorus and sulfur compounds of the type commonly used as gear lubricant additives. The deposits increase the susceptibility of the machinery to damage ad decrease the efficiency of the lubricant. I tis therefore of interest to develop improved oxidation inhibitors which decrease deposit formation in lubricants, especially gear lubricants for industrial use.

A principal object of the present invention, therefore, is to provide novel boron-containing compositions.

A further object is to provide compositions useful to improve fuel economy and extreme pressure properties and to inhibit oxidation.

A further object is to provide lubricant additives particularly adapted for use in industrial gear and bearing lubricants.

A still further object is to provide a method for preparing boron-containing compositions useful or the above-described purposes.

Other objects will in part be obvious and will in part appear hereinafter.

SUMMARY OF THE INVENTION

A method for preparing a boron-containing composition which comprises reacting, at a temperature within the range of about 70°–250° C.:

(A) at least one compound of the formula

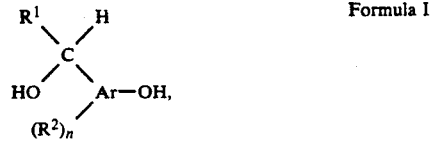

Formula I wherein $R^1$ is hydrogen, a lower alkyl-based radical or an aromatic radical, $R^2$ is hydrogen or an aliphatic hydrocarbon-based radical free from acetylenic unsaturation, n is a number from 1 to 4, and Ar is an aromatic hydrocarbon-based radical; and (B) at least one of boric acid, boron trioxide, boron halides and esters of boric acid is described.

The compositions of the invention are useful as lubricant additives to inhibit oxidation, improve extreme pressure properties and decrease fuel consumption. They are also useful as oxidation inhibitors in bear and bearing lubricants containing substantial amounts of sulfur an phosphorus compounds.

DESCRIPTION OF THE PREFERRED EMBODIMENTS

As will be apparent from the brief description hereinabove, the boron-containing composition of this invention are prepared from two reagents. Reagent A is at least one compound having Formula I. Such compounds may conveniently be prepared by the reaction of (A-1) at least one aliphatic or aromatic aldehyde-releasing compound corresponding to an aldehyde having the formula $R^1CHO$ with (A-2) at least one hydroxyaromatic compound having the formula $(R^2)_n$—ArOH.

As used in the description of these compounds, the term "hydrocarbon-based radical" denotes a radical having a carbon atom directly attached to the remainder of the molecule and having predominantly hydrocarbon character within the context of this invention. Such radicals include the following:

(1) Hydrocarbon radicals; that is, aliphatic (e.g., alkyl or alkenyl), alicyclic (e.g., cycloalkyl or cycloalkenyl), aromatic, aliphatic- and alicyclic-substituted aromatic, aromatic-substituted aliphatic and alicyclic radicals, and the like. Such radicals are known to those skilled in the art; examples are methyl, ethyl, propyl, butyl, t-butyl, hexyl, decyl, octadecyl, phenyl, tolyl, naphthyl, hexenyl, dodecenyl and octadecenyl (all isomers being included).

(2) Substituted hydrocarbon radicals; that is, radicals containing non-hydrocarbon substituents which, in the context of his invention, do not alter the predominantly hydrocarbon character of the radical. Those skilled in the art will be aware of suitable substituents; examples are halo (especially chloro and bromo), hydroxy, alkoxy, alkylthio, nitro and carbalkoxy.

(3) Hetero radicals; that is, radicals which, while predominantly hydrocarbon is character within the context of this invention, contain atoms other than carbon present in a chain or ring otherwise composed of carbon atoms. Suitable hetero atoms will be apparent to hose skilled in the art and include, for example, nitrogen, oxygen and sulfur.

In general, no more than about three substituents or hetero atoms, and preferably no more than one, will be present for each 10 carbon atoms in the hydrocarbon-based radical.

Terms such as "alkyl-based radical" and the like have meanings analogous to the above with respect to alkyl radicals and the like.

Preferably, the hydrocarbon-based radicals in the compounds of this invention are free from acetylenic and usually also form ethylenic unsaturation. The radicals are usually hydrocarbon and certain of them may be lower hydrocarbon, and word "lower" denoting radicals containing up to seven carbon atoms.

Reagent A-1, the aliphatic or aromatic aldehyde-releasing compound, may be either a free aldehyde (e.g., formaldehyde, acetaldehyde, propionaldehyde, benzaldehyde, butyraldehyde, valeraldehyde), an acetal thereof (e.g., formal, acetaldehyde diethyl acetal), or a reversible polymer thereof (e.g., trioxane, paraformaldehyde, paraldehyde). preferred as reagent A-1 are aldehyde-releasing compounds corresponding to aldehydes of the formula $R^1CHO$ in which $R^1$, is hydrogen or methyl and especially hydrogen. Thus, the preferred aldehydes are formaldehyde and acetaldehyde, especially the former.

Reagent A-2 is at least one hydroxyaromatic compound having the formula $(R^2)_n$—ArOH, in which $R^2$ may be hydrogen or an aliphatic hydrocarbon-based radical free from acetylenic unsaturation and n is a number from 1 to 4, generally 1 or 2. Most often, such as when n is 2 or 4, each $R^2$ is an alkyl group containing up to 20 carbon atoms. In such embodiments, $R^2$ may, for example, be a tert-butyl group. When n is 1, $R^2$ is a hydrocarbon-based radical containing about 4–200 and especially about 6–100 carbon atoms. More particularly, when n is 1, $R^2$ is preferably an alkyl radical containing about 4–100 or 10–100 and most desirably about 6–40 or 10–40 carbon atoms. From the standpoint of availability and particular suitability to the purposes of this invention, two types of hydroxyaromatic compounds are preferred; when n is 1, $R^2$ is preferably an alkyl group containing from about 7–30 or 15–30 carbon atoms; when n is 2 or more, each $R^2$ may contain up to 12 carbon atoms. Mixtures of the above-identified hydroxy aromatic compounds also can be used as reagent A-2. Very often commercially available alkyl phenols are mixtures of the mono-di- and tri-alkyl phenols. Some typical examples of commercial mixtures of alkyl phenols which are useful include a mixture comprising 2,4-di-tert-butyl phenol (97.5% wt.), para-tert-butyl phenol (2.0% wt.) and 2,4,6-tri-tert butyl phenol (0.5% wt.) available from Ferro Corporation under the trade designation "2,4-di-tertiary butyl phenol, 97%". Another mixture comprises 80% wt. of 2,4-di-tert-butyl phenol, 7–8% wt. of 2,4,6-tri-tert-butyl phenol, 7–8% wt. of para tert-butyl phenol, 1% of ortho tert-butyl phenol, and 1% wt. max of phenol.

The Ar radical is an aromatic hydrocarbon-based radical, typically derived form such aromatic compounds as benzene, naphthalene, biphenyl, diphenylmethane and diphenyl sulfide. Thus, the hydroxyaromatic compound may be, for example, phenol, a naphthol, an alkylphenol, dialkyl or trialkyl phenol, or alkylnaphthol, or a sulfur- and/or methylene-bridged phenol or alkylphenol. Suitable sulfur-bridged phenols may be prepared by the reaction of sulfur dichloride with the corresponding phenol or alkylphenol. Methylene-bridged phenols may be prepared by a similar reaction with a formaldehyde-releasing reagent, which may be at the same time as the reaction with reagent A-1 (which is, of course, preferably also a formaldehyde-releasing reagent) or before or after that reaction.

The alkylphenols represented by the formula

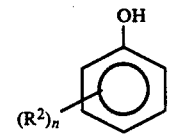

Formula II and mixtures thereof are preferred for use as reagent A-2, and especially those containing at least one unsubstituted ortho or para carbon atom, preferably ortho. Especially preferred are compounds in which Ar is a phenylene radical (i.e., —$C_6H_4$—) and most desirably o-phenylene. Such compounds are typically prepared by the known alkylation of phenols with various olefins, alkyl halides and the like, including commercial mixtures of such olefins and alkyl halides.

By convention, the "Ar" radical includes within its structure all hydrogen atoms bonded directly to an aromatic ring. Thus, all aromatic carbon atoms not bonded to some to her part of the molecule or to a substituent, specified or unspecified, are understood to be bonded to hydrogen atoms.

The reaction of reagents A-1 and A-2 is a known reaction; it is frequently effected in the presence of an acidic or basic catalyst. The acidic catalyst may, for example, be an alkanoic acid. Reactions of this type are disclosed, for example, in U.S. Pat. No. 4,147,643, which is incorporated by reference herein for such disclosure.

Reagent B is the method of this invention is at least one of boric acid, boron trioxide ($B_2O_3$), boron halides (especially boron trichloride, $BCl_3$), boron halides (especially boron trichloride, $BCl_3$) and esters of boric acid. Boron trioxide will react first and with water formed in the reaction of reagents A-1 and A-2 to form boric acid, which then reacts further. Any of the various forms of boric acid may be used, including metaboric acid ($HBO_2$), orthoboric acid ($H_3BO_3$) and tetraboric acid ($H_2B_4O_7$). The esters of these acids include, for example, the methyl, ethyl and propyl esters, with the methyl esters being most readily available and therefore most often used. Boric acid, and especially orthoboric acid, is preferred for use as reagent B.

The method of this invention involves reacting reagents A and B at a temperature within the range of about 70°–250° C., preferably about 90°–150° and most often about 90°–130° C. It is often preferred to form reagent A in situ by heating a mixture of reagents A-1, A-2 and B. The reaction si frequently effected in the presence of a substantially inert, normally liquid organic diluent, typically an aromatic hydrocarbon such as toluene or xylene, a chlorinated aromatic hydrocarbon such as chlorobenzene or an ether such as ethylene glycol dimethyl ether.

When formaldehyde or a formaldehyde-releasing compound is sued as reagent A-1, a portion thereof is sometimes lost by volatilization during the reaction. It is therefore preferred to sue reagent A-1 in excess. Most often, about 1.5–8.0 moles of reagent A-1 and about 1.0–2.5 moles of reagent A-2 are used per mole of reagent B.

The reaction of A-1, A-2 and B is frequently effected in the presence of (C), a catalyst. It has been observed, however, that the reaction will proceed without a catalyst. Suitable acidic catalysts include acid-form anion exchange resins, sulfonic acids such as benzene-sulfonic and p-toluene-sulfonic acids, and alkanoic acids such as acetic, propionic, butyric and valeric acids. The lower alkanoic acids and especially propionic acid are preferred. The amount of reagent C is typically less than 0.5 mole, most often about 0.1–0.3 mole, per mole or reagent A-1. Examples of bases useful as catalysts include inorganic bases such as the alkali metal hydroxides.

The molecular structures of the boron-containing compositions prepared by the method of this invention are not known with certainty. Most likely, they are mixtures of compounds having a number of molecular structures. However, there is strong evidence of the presence therein of compounds having the formula

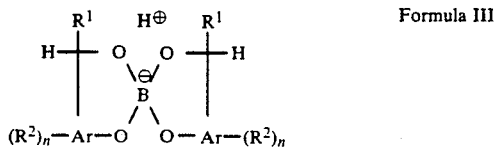

Formula III wherein $R^1$, $R^2$, n and Ar are as previously defined. Therefore, the present invention also includes boron-containing compositions comprising at least one compound having Formula II.

The preparation of the boron-containing compositions of this invention is illustrated by the following examples. All parts and percentages are by weight unless otherwise indicated.

EXAMPLE 1

A mixture of 485.7 grams (1 mole) of an alkyl phenol prepared by alkylation of phenol with a commercial mixture of $C_{24-28}$ alpha-olefins, 10 grams (1 mole) of paraformaldehyde, 30.9 grams (0.5 mole) of boric acid, 22.2 grams (0.3 mole) of propionic acid and 600 ml. of toluene is heated under reflux for thee hours, as water is removed by distillation. An additional ten grams of paraformaldehyde is added and refluxing is continued for two hours; a third ten-ram portion of paraformaldehyde (total 3 moles) is then added and refluxing is continued as water and excess paraformaldehyde are removed. A total of 45 ml. of water is obtained. The mixture is filtered and vacuum stripped to yield the desired product, which contains 1.19% boron.

EXAMPLE 2

A product similar to that of Example 1 is obtained from 1,094 grams (2 moles) of the alkylphenol of Example 1, 120 grams (4 moles) of paraformaldehyde added in two 60-gram increments, 123.6 grams (2 moles) of boric acid, 44.4 grams (0.6 mole) of propionic acid and 700 ml. of toluene. It contains 1.32% boron.

EXAMPLE 3

A mixture of 1,094 parts (2 moles) of the alkylphenol of Example 1, 60 parts (2 moles) of paraformaldehyde, 68.8 parts (1 mole) of boric acid, 44.4 parts (0.6 mole) of propionic acid and 200 parts of toluene is heated under reflux for about 6 hours as water (about 70 parts) is removed by distillation. The mixture is then vacuum stripped and filtered at 110°–120° C. to yield the desired product; it contains 0.73% boron.

EXAMPLE 4

A mixture of 536 parts (1 mole) of the alkylphenol of Example 1, 30 parts (1 mole) of paraformaldehyde, 30.9 parts (0.5 mole) of boric acid and 100 parts of toluene is heated under reflux for 3 hours as water is removed by distillation. A second 30-part increment of paraformaldehyde (total 2 moles) is added and heating under reflux is continued for 5 hours. A total of 48 ml. of water is removed. The mixture is then vacuum stripped and filtered while hot to yield the desired product; it contains 0.89% boron.

EXAMPLE 5

Following the procedure of Example 1, a product containing 1.75% boron is obtained by the reaction of 792 grams (3 moles) of tetrapropenylphenol, 270 grams (9 moles, added in three 3-mole increments of paraformaldehyde, 92.7 parts (1.5 moles) of boric acid, 66.6 parts (0.9 mole) of propionic acid and 1,000 ml. of toluene.

EXAMPLE 6

A mixture of 430 parts (1 mole) of an alkylphenol prepared by alkylation of phenol with a commercial mixture of $C_{18-24}$ alpha-olefins, 30 parts (1 mole) of paraformaldehyde, 30.9 parts (0.5 mole) of boric acid, 22.2 parts (0.3 mole) of propionic acid and 100 parts of toluene is heated under reflux as water is removed by distillation. After 33 ml. of water have been removed, an additional 30 parts of paraformaldehyde is added (total 2 moles) and refluxing is continued as water (total 41 ml.) and paraformaldehyde are removed by distillation. The mixture is vacuum stripped and filtered to yield the desired product; it contains 1.14% boron.

EXAMPLE 7

A mixture of 1,945 parts (5 moles) of an alkylphenol prepared by alkylation of phenol with a decene dimer, 150 parts (5 moles) of paraformaldehyde, 154 parts (2.5 moles) of boric acid, 88.8 parts (1.2 moles) of propionic acid and 300 parts of toluene is heated under reflux as water is removed by distillation. When 157 parts of water has been removed, an additional 150 parts of paraformaldehyde is added (total 10 moles) and heating is continued until water evolution is complete. The mixture is vacuum stripped and filtered while hot. The filtrate is the desired product; it contains 1.44% boron.

EXAMPLE 8

A boron-containing composition is prepared by a method similar to that of Example 1 except that trimethyl borate is substituted, on an equimolar basis, of the boric acid.

EXAMPLE 9

A boron-containing composition is prepared by a method similar to that of Example 1 except that paraldehyde and acetic acid are respectively substituted, on an equimolar basis, for the paraformaldehyde and propionic acid.

EXAMPLE 10 a mixture of 206.3 grams of 2,4-di-tert-butyl phenol (1 mole), 30.9 grams (0.5 mole) of boric acid, 22.2 grams (0.3 mole) of propionic acid, 150 ml. of toluene and 30 grams (1 mole) of paraformaldehyde is charged to a reaction flask and heated to reflux with collection of 28 ml. of water. A second 30 grams of paraformaldehyde is added and refluxing continued with removal of a small amount of water and a larger amount of paraformaldehyde. The reaction mixture is filtered through filter acid and the filtrate is stripped at 200° C./25 m. Hg. to yield the desired product containing 2.17% boron.

EXAMPLE 11

A mixture of 824 grams (4 moles) of 2,4-di-tert-butyl phenol, 80% (Ferro Corporation), 180 grams (6 moles) of paraformaldehyde, 123.6 grams (2 moles) of boric acid and 300 grams of toluene is charged to a reactor and heated to reflux with removal of water (191 grams of water removed). Diluent oil (960 grams) is added and the mixture is stripped at 150° C./25 mm. Hg. The residue is filtered, and the filtrate is the desired product containing 1.24% boron.

EXAMPLE 12

A mixture of 619 grams (3 moles) of 2,4-di-tert-butyl phenol, 97% (Ferro Corporation), 90 grams (3 moles) of paraformaldehyde, 92.7 grams (1.5 moles) of boric, 33.3 grams of propionic acid and 250 grams of toluene are charged to a reactor and heated to reflux while removing water (88 ml. collected). A second 90 grams of paraformaldehyde is added and refluxing was continued up to 140° C. with removal of solid paraformaldehyde. Diluent oil (720 grams) is added an the mixture is stripped at 175° C./30 mm. The residue is filtered warm and the filtrate is the desired product containing 1.23% boron.

EXAMPLE 13

A mixture of 619 grams (3 moles ) of the 2,4-di-tert-butyl phenol used in Example 12, 135 grams (4.5 moles) of paraformaldehyde, 92.7 grams (1.5 moles) of boric acid and 250 grams of toluene are charged to a reactor and heated to reflux while removing water (139 ml. of water recovered). Diluent oil (720 grams) is added to the reactor, and the mixture is stripped at aspirator to 150° C. The residue is the desired product containing 1.23% of boron.

EXAMPLE 14

A mixture of 1030 parts of 2,6-di-t-butyl phenol and 1145 parts of a mixture of alpha-olefins containing 15 to 18 carbon atoms is charged to a reactor and 109 parts of Superfiltrol is added at 40° C. The reaction mixture is heated to 85°-90° C. and maintained at the temperature for about 2.5 hours followed by heating at 130°-140° C. for an additional two to five hours. The mixture then is filtered through a filteraid, and the filtrate is returned to the reaction flask where volatiles are stripped at 140° C./5 mm. Hg. The residue is filtered, and the filtrate is the desired alkylated, t-butyl phenol.

A mixture of 920 parts of the above-prepared alkylated, t-butyl phenol product, 90 of paraformaldehyde, 62 parts of boric acid, 45 parts of propionic acid, and 500 parts of toluene is charged to a reactor and the mixture is heated to reflux for three hours to a temperature of 130°-135° C. Water, excess paraformaldehyde and toluene is removed in a side-arm trap. The crude material is stripped at 135°-140° C./10 mm. Hg. and filtered. The filtrate is the desired product.

EXAMPLE 15

A mixture of 1030 parts of 2,6-di-t-butyl phenol and 725 parts of a polypropylene tetramer (molecular weight of 145) is charged to a reactor and heated to about 40° C. whereupon 88 parts of Suprafiltrol is added. The reaction is conducted in a nitrogen atmosphere. The temperature of the reaction is raised to 145°-150° C. and thereafter maintained at 90°-95° C. at 5 mm. Hg. for about 3.5-4 hours while collecting water in a side-arm trap. The reaction mixture is filtered, and the filtrate is the desired alkylated t-butyl phenol.

A mixture of 600 parts of the above-prepared alkylated t-butyl phenol, 120 parts of paraformaldehyde, 62 parts of boric acid, 22 parts of propionic acid and 500 parts of toluene is charged to a reactor and heated to reflux for three hours to a temperature of about 130°-135° C. while collecting a mixture of water, excess paraformaldehyde and toluene. The crude mixture is stripped to 140° C./10 mm. Hg. and filtered. The filtrate is the desired boron-containing product.

EXAMPLE 16

A mixture of 206 parts of 2,4-di-t-butyl phenol, 30 parts of paraformaldehyde and 0.5 parts of sodium hydroxide is heated to 130° C., and 31 parts of boric acid is added while sparging with nitrogen. The mixture then is heated at 110°-170° C. for one hour while removing water. The mixture is vacuum stripped to 160° C. at 30-40 mm. Hg., 241 parts of mineral oil are added, and the mixture is filtered. The filtrate is the desired product containing 0.94% of boron.

As previously indicated, the boron-containing compositions of this invention are useful as additives for lubricants. They are particularly useful as oxidation inhibitors and extreme pressure agents in gear and bearing lubricants; however, they may also be used in internal combustion engine lubricants to reduce fuel consumption. They can be employed in a variety of lubricants based on diverse oils of lubricating and grease viscosity, including natural and synthetic lubricating oils and mixtures thereof. In addition to gear and bearing lubricants, the boron-containing compositions may be used in crankcase lubricating oils for spark-ignited and compression-ignited internal combustion engines, including automobile and truck engines, two-cycle engines, aviation piston engines, marine and railroad diesel engines, and the like. The boron-containing compositions can also be sued in gas engines, stationary power engines and turbines and the like. Automatic transmission fluids, transaxle lubricants, metalworking lubricants, hydraulic fluids and other lubricating oil and grease composition can also benefit from the incorporation therein of the boron-containing compositions.

Natural oil include liquid petroleum oils and solvent-treated, acid-treated and/or hydrorefined mineral lubricating oils of the paraffinic, naphthenic and mixed paraffinic-naphthenic types. Oils of lubricating viscosity derived form coal or shale are also useful base oils.

Synthetic lubricating oils include hydrocarbon oils and halo-substituted hydrocarbon oils such as polymerized and interpolymerized olefins [e.g., polybutylenes, polypropylenes, propylene-isobutylene copolymers, chlorinated polybutylene, poly(1-hexenes), poly(1-octenes), poly(1-decenes)]; alkylbenzenes [e.g., dodecylbenzenes, tetradecylbenzenes, dinonylbenzenes, di(2-ethylhexyl)benzenes]; polyphenyls (e.g., biphenyls, terphenyls, alkylated polyphenyls); and alkylated diphenyl ethers and alkylated diphenyl sulfides and the derivatives, analogs and homologs thereof. neopentyl glycol, trimethylolpropane, pentaerythritol, dipentaerythritol and tripentaerythritol.

Silicon-based oils such as the polyalkyl-, polyaryl-, polyalkoxy-, or polyaryloxysiloxane oils and silicate oils comprise another useful class of synthetic lubricants; they include tetraethyl silicate, tetra-isopropyl silicate, tetra-(2-ethylhexyl) silicate, tetra-(4-methyl-2-ethylhexyl) silicate, tetra-(p-tert-butylphenyl) silicate, hexa-(4-methyl-2-pentoxy)disiloxane, poly(methyl)siloxanes and poly(methylphenyl)siloxanes. Other synthetic lubricating oils include liquid esters of phosphorus-containing acids (e.g., tricresyl phosphate, trioctyl phosphate, diethyl ester of decylphosphonic acid) and polymeric tetrahydrofuran.

Unrefined, refined and rerefined oils can be used in the lubricants of the preset invention. Unrefined oils are those obtained directly from a natural or synthetic source without further purification treatment. For example, a shale oil obtained directly from retorting operations, a petroleum oil obtained directly form distillation or ester oil obtained directly for an esterification process and used without further treatment would be an unrefined oil Refined oils are similar to the unrefined oils except they have been further treated in one or more purification steps to improve one or more properties. Many such purification techniques, such as distillation, solvent extraction, acid or base extraction, filtration and percolation are known to those skilled in the art. Rerefined oils are obtained by processes similar to those used to obtain refined oils applied to refined oils which have been already used in service. Such rerefined oils are also known as reclaimed or reprocessed oils and often are additionally processed by techniques for removal of spent additives and oils breakdown products. Alkylene oxide polymers and interpolymers and derivatives thereof where the terminal hydroxyl groups have been modified by esterification, esterification, etc., constitute another class of known synthetic lubricating oils. These are exemplified by polyoxyalkylene polymers prepared by polymerization of ethylene oxide or propylene oxide, the alkyl and aryl ethers of these polyoxyalkylene polymers (e.g., methylpolyisopropylene glycol ether having an average molecular weight of 1000, diphenyl ether of polyethylene glycol having a molecular weight of 500–1000, diethyl ether of polypropylene glycol having a molecular weight of 1000–1500); and mono- and polycarboxylic esters thereof, for example, the acetic acid esters, mixed $C_3$–$C_8$ fatty acid esters and $C_{13}$ Oxo acid diester of tetraethylene glycol.

Another suitable class of synthetic lubricating oils comprises the esters of dicarboxylic acid (e.g., phthalic acid, succinic acid, alkyl succinic acids and alkenyl succinic acids, maleic acid, azelaic acid, suberic acid, sebacic acid, fumaric acid, adipic acid, linoleic acid dimer, malonic acid, alkyl malonic acids, alkenyl malonic acids) with a variety of alcohols (e.g., butyl alcohol, hexyl alcohol, dodecyl alcohol, 2-ethylhexyl alcohol, ethylene glycol, diethylene glycol monoether, propylene glycol). Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, and the complex ester formed by reacting one mole of sebacic acid with two moles of tetraethylene glycol and two moles of 2-ethyl-hexanoic acid.

Esters useful as synthetic oils also include those made form $C_5$ to $C_{12}$ monocarboxylic acids and polyols and polyol ethers such as Generally, the lubricants of the present invention contain an amount of the boron-containing compositions sufficient to inhibit oxidation, improve extreme pressure properties or decrease fuel consumption. Normally this amount will be about 0.1–5.0% by weight.

The invention also contemplates the use of other additives in combination with the boron-containing compositions. Suitable additives for internal combustion engine lubricants include, for example, detergents and dispersants of the ash-producing or ashless type, corrosion-inhibiting and auxiliary oxidation-inhibiting agents, pour point depressing agents, extreme pressure agents, color stabilizer sand anti-foam agents.

The ash-producing detergents are exemplified by oil-soluble neutral and basic salts of alkali or alkaline earth metals with sulfonic acids, carboxylic acids, and organic phosphorus acids characterized by at least one direct carbon-to-phosphorus linkage including those prepared by the treatment of the an olefin polymer (e.g., polyisobutene having a molecular weight of 1000) with a phosphorizing agent such as phosphorus trichloride, phosphorus heptasulfide, phosphorus pentasulfide, phosphorus trichloride and sulfur, white phosphorus and a sulfur halide, or phosphorothioic chloride. The most commonly used slats of such acids are those of sodium, potassium lithium, calcium, magnesium, strontium and bariums.

The term "basic salt" is used to designate metal salts wherein the metal is present in stoichiometrically larger amounts than the organic acid radical. The commonly employed methods for preparing the basic salts involve heating a mineral oil solution of an acid with a stoichiometric excess of a metal neutralizing agent such as the metal oxide, hydroxide, carbonate, bicarbonate, or sulfide at a temperature above 50° C. and filtering the resulting mass. The use of a "promoter" in the neutralization step to aid the incorporation of a large excess of metal likewise is known. Examples of compounds useful as the promoter include phenolic substances such as phenol, naphthol, alkylphenols, thiophenol, sulfurized alkylphenols, and condensation products of formaldehyde with phenoic substances; alcohols such as methanol, 2-propanol, octyl alcohol, Celosolve, Carbitol, ethylene glycol, stearyl alcohol and cyclohexyl alcohol; and amines such as aniline, phenylenediamine, phenothiazine, phenyl-beta-naphthylamine and dodecylamine. A particularly effective method for preparing the basic salts comprises mixing an acid with an excess of a basic alkaline earth metal neutralizing agent and at least one alcohol promoter, and carbonating the mixture at an elevated temperature such as 60°–200° C.

Ashless detergents and dispersant are so called despite the fact that, depending on its constitution, the dispersant may upon combustion yield a non-volatile material such as boric oxide or phosphorus pentoxide; however, it does not ordinarily contain metal and therefore does not yield a metal-containing ash on combustion. Many types are known in the art, and any of them are suitable for use in the lubricants of this invention. The following are illustrative:

(1) Reaction products of carboxylic acids (or derivatives thereof) containing at least about 34 and preferably at least about 54 carbon atoms with nitrogen-containing compounds such as amine, organic hydroxy compounds such as phenols and alcohols, and/or basic inorganic materials. Examples of these "carboxylic dispersants" are describe din many U.S. Patents including U.S. Pat. Nos. 3,272,746; 3,381,022; and 4,234,435.

(2) Reaction products of relatively high molecular wight aliphatic or alicyclic halide with amines, preferably polyalkylene polyamines. These may be characterized as "amine dispersants" and examples thereof are described for example, in U.S. Pat. Nos. 3,275,554; 3,438,757; 3,454,55; and 3,565,804.

(3) Reaction products of alkylphenols in which the alkyl group contains at least about 30 carbon atoms with aldehydes (especially formaldehyde) and amine (especially polyalkylene polyamines), which may be characterized as "Mannich dispersants". The materials described in U.S. Pat. Nos. 3,368,972; 3,413,347; and 3,980,569 are illustrative.

(4) Products obtained by post-treating the carboxylic, amine or Mannich dispersants with such reagents as urea, thiourea, carbon disulfide, aldehydes, ketones, carboxylic acids, hydrocarbon-substituted succinic anhydrides, nitriles, epoxides, boron compounds, phosphorus compounds or the like. Exemplary materials of this kind are described in a number of U.S. patents.

(5) Interpolymers of oil-solubilizing monomers such as decyl methacrylate, vinyl decyl ether and high molecular wight olefins with monomers containing polar substituents, e.g., amino alkyl acrylates or acrylamides and poly-(oxyethylene)-substituted acrylates. These may be characterized as "polymeric dispersants" and examples thereof are disclosed in U.S. Pat. Nos. 3,329,658; 3,449,250; 3,519,565; 3,666,730; 3,687,849; and 3,702,300.

All of the above-noted patents are incorporated by reference herein for their disclosures of ashless dispersants.

Extreme pressure agents and corrosion-inhibiting and auxiliary oxidation-inhibiting agents are exemplified by chlorinated aliphatic hydrocarbons such as chlorinated was; organic sulfides and polysulfides such as benzyl disulfide, bis(chlorobenzyl)disulfide, dibutyl tetrasulfide, sulfurized methyl oleate, sulfurized alkylphenols, sulfurized dipentene, and sulfurized terpenes; phosphosulfurized hydrocarbons such as the reaction product of a phosphorus sulfide with turpentine or methyl oleate; phosphorus esters including principally dihydrocarbon and trihydrocarbon phosphites such as dibutyl phosphite, diheptyl phosphite, dicyclohexyl phosphite, pentyl-phenyl phosphite, dipentylphenyl phosphite, tridecyl phosphite, distearyl phosphite, dimethylnaphthyl phosphite, oleyl 4-pentylphenyl phosphite, polypropylene (molecular weight 500)-substituted phenyl phosphite and diisobutyl-substituted phenyl phosphite; metal thiocarbamates such as zinc dioctyldithiocarbamate and barium heptylphenyl dithiocarbamate; Group II metal phosphorodithioates such as zinc dicyclohexylphosphorodithioate, zinc dioctylphosphorodithioate, barium di(heptylphenyl)phosphorodithioate, cadmium dinonylphsophorodithioate, and the zinc salt of a phosphorodithioic acid produced by the reaction of phosphorus pentasulfide with an equimolar mixture of isopropyl alcohol and n-hexyl alcohol.

Gear and bearing lubricants according to this invention may contain the boron-containing compositions in combination with known gear lubricant additive packages. These packages frequently contain substantial amounts, effective to improve the extreme pressure properties thereof, of sulfur and phosphorus compounds. Many suitable gear lubricant additive packages of this type are known to those skilled in the art. The boron-containing compositions are particularly effective as oxidation inhibitors in such lubricants containing relatively high sulfur nd phosphorus levels.

The boron-containing compositions of this invention may be, and frequently are, added directly to the otherwise fully formulated lubricant prior to use. However, they may also be diluted with a substantially inert, normally liquid organic diluent such as mineral oil naphtha, benzene, toluene or xylene to form an additive concentrate. These concentrates may contain from about 10% to about 90% by weight of the boron-containing composition and may contain, in addition, one or more other additives known in the art or described hereinabove. The additive concentrate may, for example, comprise a substantially inert, normally liquid organic diluent and abut 20-90% by weight of the boron-containing composition.

The following table contains examples of gear and bearing lubricants of this invention. All parts are by weight.

| Lubricant Examples | 1* | 2 | 3 |
|---|---|---|---|
| Mineral oil | 97.89 | 97.83 | 98.06 |
| Product of Example 1 | 0.75 | — | — |
| Product of Example 10 | — | 0.75 | — |
| Product of Example 11 | — | — | 0.50 |
| Polyisobutenyl succinic anhydride-ethylene polyamine reaction product | — | — | 0.05 |
| Oleamide/linoleamide mixture | — | — | 0.03 |
| Soybean oil | 0.25 | 0.25 | — |
| Sulfurized isobutene | 0.62 | 0.687 | 0.95 |
| Amine-neutralized phosphate ester of hydroxylalkyl dialkylphosphorodithioate | 0.40 | 0.40 | 0.26 |
| Polyoxyalkylene demulsifier | 0.005 | 0.005 | 0.005 |
| N-Tridecyltrimethylenediamine | 0.05 | 0.05 | 0.05 |
| Tolyltrizaole | 0.015 | 0.015 | — |
| Mixed tertiary alkyl($C_{11-14}$) aliphatic primary amine | — | — | 0.04 |
| Reaction product of alkyl phenol, formaldehyde and dimercapto thiadiazole | — | — | 0.04 |
| Silicone anti-foam agent | 0.02 | 0.02 | 0.02 |

*parts by weight

What is claimed is:

1. A lubricant comprising a major amount of an oil of lubricating oil viscosity and about 0.1-5.0% by weight of a boron-containing composition which is the product obtained by the process of reacting, at a temperature within the range of about 70°-250° C.;

(A) at least on compound of the formula

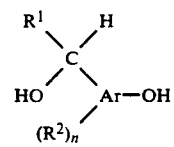

wherein $R^1$ is hydrogen, a lower alkyl-based radical or an aromatic hydrocarbon-based radical, $R^2$ is hydrogen or an aliphatic hydrocarbon-based radical free form acetylenic unsaturation, n is a number from 1 to 4, and Ar is an aromatic hydrocarbon-based radical; and (B) at least one of boric acid, boron trioxide, boron halides and esters of boric acid.

2. The lubricant according to claim 1, wherein reagent A is formed in situ by the reaction of (A-1) at least one aromatic or aliphatic aldehyde-releasing compound corresponding to an aldehyde having the formula $R^1CHO$ with (A-2) at least one hydroxyaromatic compound having the formula $(R^2)_n$—Ar—OH.

3. The lubricant according to claim 2 wherein Ar contains at least one unsubstituted ortho or para carbon atom.

4. The lubricant according to claim 3 wherein Ar contains at least one unsubstituted ortho carbon atom.

5. The lubricant according to claim 3 wherein Ar is a phenylene radical.

6. The lubricant according to claim 5 wherein Ar is an o-phenylene radical.

7. The lubricant according to claim 6 wherein $R^1$ is hydrogen or methyl.

8. The lubricant according to claim 1 wherein n is a number from 2 to 4 and each $R^2$ is an alkyl radical containing up to about 20 carbon atoms.

9. The lubricant according to claim 7 wherein n is a number from 2 to 4 and each $R^2$ is an alkyl radical containing up to 20 carbon atoms.

10. The lubricant according to claim 1 wherein $R^2$ is a tert-butyl group.

11. The lubricant according to claim 1 wherein the reaction of reagent A and reagent B is carried out in the presence of:
(C) an acidic or basic catalyst.

12. The lubricant according to claim 11 wherein reagent A is formed in situ by the reaction of (A-1) at least one aromatic or aliphatic aldehyde-releasing compound corresponding to an aldehyde having the formula $R^1CHO$ with (A-2) at least one hydroxyaromatic compound having the formula $(R^2)_n$—Ar—OH.

13. The lubricant according to claim 11 wherein Ar contains at least one unsubstituted ortho carbon atom.

14. The lubricant according to claim 11 wherein n is a number from 2 to 4 and each $R^2$ is an alkyl radical containing up to 20 carbon atoms.

15. The lubricant according to claim 11 wherein C is an acid catalyst.

16. The lubricant according to claim 11 wherein is an alkanoic acid.

17. The lubricant according to claim 11 wherein C is a base.

18. The lubricant according to claim 1 wherein the lubricant further comprises a minor amount, effective to improve the extreme pressure properties thereof, of compounds containing sulfur or phosphorus or a combination of sulfur and phosphorus.

19. The lubricant according to claim 18 wherein n is a number from 2 to 4 and each $R^2$ is an alkyl radical containing up to about 20 carbon atoms.

20. The lubricant according to claim 19 wherein $R^1$ is hydrogen or methyl.

21. The lubricant according to claim 18 wherein $R^2$ is a tert-butyl group.

22. The lubricant according to claim 18 wherein the boron-containing composition is present in an amount in the range of about 0.1-5.0% by weight of the lubricant.

23. A method for lubricating an internal combustion engine comprising:
using a lubricant according to claim 1 to lubricate the internal combustion engine.

24. The method according to claim 23 wherein $R^1$ is hydrogen or methyl, n is a number from 2 to 4 and each $R^2$ is an alkyl radical containing up to 20 carbon atoms.

25. The method according to claim 24 wherein each $R^2$ is a tert-butyl group.

26. A method for preparing a boron-containing lubricant comprising:
preparing a boron-containing composition which is the product obtained by the process of reacting, at a temperature within the range of about 70°-250° C.:
(A) at least one compound of the formula

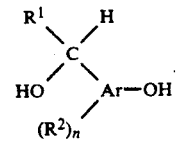

wherein $R^1$ is hydrogen, a lower alkyl-based radical or an aromatic hydrocarbon-based radical, $R^2$ is hydrogen or an aliphatic hydrocarbon-based radical free form acetylenic unsaturation, n is a number from 1 to 4, and Ar is an aromatic hydrocarbon-based radical; and (B) at least one of boric acid, boron trioxide, boron halides and esters of boric acid, and
adding the boron-containing composition to an oil of lubricating oil viscosity in an amount in the range from about 0.1-5.0% by weight.

27. The method of claim 26 wherein the step of adding the boron-containing composition includes
preparing an additive concentrate comprising a substantially inert, normally liquid organic diluent and about 20-90% by weight of the boron-containing composition and
adding the additive concentrate to the oil of lubricating oil viscosity.

28. The method according to claim 26 wherein reagent A is formed in situ by the reaction of (A-1) at least one aromatic or aliphatic aldehyde-releasing compound corresponding to an aldehyde having the formula $R^1CHO$ with (A-2) at least one hydroxyaromatic compound having the formula $(R^2)_n$—Ar—OH.

29. The method according to claim 28 wherein about 1.5-8.0 moles of reagent A-1 and about 1.0-2.5 moles of regent A-2 are used per mole of reagent B.

30. The method according to claim 26 wherein n is a number from 2 to 4 and each $R^2$ is an alkyl radical containing up to about 20 carbon atoms.

31. The method according to claim 26 wherein $R^1$ is hydrogen or methyl, n is a number from 2 to 4 and each $R^2$ is an alkyl radical containing up to 20 carbon atoms.

32. The method according to claim 32 wherein each $R^2$ is a tert-butyl group.

* * * * *